US010786140B2

(12) United States Patent
Yasuda et al.

(10) Patent No.: US 10,786,140 B2
(45) Date of Patent: Sep. 29, 2020

(54) ENDOSCOPE HAVING OPERATION WIRE WITH STRETCHABLE COATING MEMBER

(71) Applicant: FUJIFILM Corporation, Tokyo (JP)

(72) Inventors: Hiroaki Yasuda, Kanagawa (JP);
Tomohiro Ohki, Kanagawa (JP);
Satoru Ogami, Kanagawa (JP);
Toshizumi Tanaka, Kanagawa (JP);
Tatsuya Minagawa, Kanagawa (JP);
Takashi Harada, Kanagawa (JP);
Shozo Iyama, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 370 days.

(21) Appl. No.: 15/706,772

(22) Filed: Sep. 18, 2017

(65) Prior Publication Data
US 2018/0078121 A1 Mar. 22, 2018

(30) Foreign Application Priority Data
Sep. 21, 2016 (JP) .................................. 2016-184553

(51) Int. Cl.
*A61B 1/00* (2006.01)
*A61B 1/018* (2006.01)
*A61B 1/005* (2006.01)

(52) U.S. Cl.
CPC ...... *A61B 1/00098* (2013.01); *A61B 1/00101* (2013.01); *A61B 1/00133* (2013.01);
(Continued)

(58) Field of Classification Search
CPC ............ A61B 1/00098; A61B 1/00101; A61B 1/00133; A61B 1/018
See application file for complete search history.

(56) References Cited

U.S. PATENT DOCUMENTS 3,915,157 A * 10/1975 Mitsui ................ A61B 1/00098
600/107
2010/0191150 A1 * 7/2010 Palme, Jr. ............. A61M 25/09
600/585
(Continued)

FOREIGN PATENT DOCUMENTS

JP H04312438 11/1992
JP H05123288 5/1993
(Continued)

OTHER PUBLICATIONS

Office Action of Europe Counterpart Application, dated Oct. 26, 2018, pp. 1-4.
(Continued)

*Primary Examiner* — Timothy J Neal
*Assistant Examiner* — William B Chou
(74) *Attorney, Agent, or Firm* — JCIPRNET

(57) ABSTRACT

An endoscope includes a standing base in a tip portion body, an operation wire of which a tip side is connected to the standing base, and a stretchable coating member that covers the operation wire along an extending direction of the operation wire and so as to allow the operation wire to be relatively movable over the entire region from a connection portion between the standing base and the operation wire to an operation wire-guide passage. A tip of the coating member and the standing base are liquid-tightly fixed to each other, and a base end of the coating member and the operation wire-guide passage are liquid-tightly fixed to each other, and the coating member is disposed at a position where a moving path of the coating member and a moving path of a treatment tool led from a treatment tool-guide passage do not interfere with each other.

15 Claims, 13 Drawing Sheets

(52) U.S. Cl.
CPC .......... *A61B 1/00177* (2013.01); *A61B 1/018* (2013.01); *A61B 1/0057* (2013.01)

(56) References Cited

U.S. PATENT DOCUMENTS

| | | | |
|---|---|---|---|
| 2011/0190865 A1* | 8/2011 | McHugo | A61F 2/95 623/1.11 |
| 2015/0250992 A1* | 9/2015 | Morriss | A61M 29/02 606/198 |
| 2016/0081702 A1* | 3/2016 | Kan | A61B 17/221 606/113 |
| 2017/0000312 A1* | 1/2017 | Kakehashi | A61B 1/0051 |
| 2017/0020370 A1 | 1/2017 | Yamaya | |
| 2017/0119414 A1* | 5/2017 | Chan | A61B 17/24 |
| 2018/0035869 A1 | 2/2018 | Yamaya | |

FOREIGN PATENT DOCUMENTS

| | | |
|---|---|---|
| JP | H06315457 | 11/1994 |
| JP | H0759730 | 3/1995 |
| JP | H09299315 | 11/1997 |
| WO | 2016027574 | 2/2016 |
| WO | 2017002587 | 1/2017 |

OTHER PUBLICATIONS

"Search Report of Europe Counterpart Application", dated Jan. 2, 2018, p. 1-p. 7, in which the listed references were cited.

* cited by examiner

ENDOSCOPE HAVING OPERATION WIRE WITH STRETCHABLE COATING MEMBER

CROSS-REFERENCE TO RELATED APPLICATIONS

The present application claims priority under 35 U.S.C. § 119 to Japanese Patent Application No. 2016-184553, filed on Sep. 21, 2016. The above application is hereby expressly incorporated by reference, in its entirety, into the present application.

BACKGROUND OF THE INVENTION

1. Field of the Invention

The present invention relates to an endoscope that includes a standing base (elevator) provided on the tip side of an insertion unit and changing the lead-out direction of a treatment tool.

2. Description of the Related Art

Various treatment tools are introduced into an endoscope from a treatment tool inlet provided in an operation unit, and the treatment tools are led from a treatment tool outlet opened to a tip portion of an insertion unit to the outside and are used for treatment. For example, a treatment tool, such as a guide wire or an imaging tube, is used in a duodenoscope. A treatment tool, such as a puncture needle, is used in an ultrasonic endoscope. A treatment tool, such as forceps or a snare, is used in other endoscopes, such as a direct-view endoscope and an oblique endoscope. The lead-out direction of such a treatment tool needs to be changed at the tip portion so that treatment is performed at a desired position in a subject. For this purpose, a standing base, which changes the lead-out direction of a treatment tool, is provided at the tip portion. Further, an endoscope is provided with a treatment tool-standing mechanism that changes the posture of the standing base between a standing position and a falling position.

A wire tugging (open type) mechanism in which the tip of an operation wire is directly mounted on a standing base is known as the treatment tool-standing mechanism. The mechanism connects the base end of the operation wire to an operation lever of an operation unit, rotates the standing base about a rotation axis by pushing and pulling the operation wire with the operation lever, and changes the posture of the standing base between a standing position and a falling position.

Whenever an endoscope is used for various kinds of examination or treatment, the endoscope needs to be subjected to washing-antiseptic treatment using a washing solution and an antiseptic solution. For the easy washing of the endoscope including the treatment tool-standing mechanism, JP1993-123288A (JP-H05-123288A) discloses a technique that connects an operation wire to the vicinity of the tip of a treatment tool-insertion channel and moves forward and backward the operation wire in a water-tightly sealed rubber cover.

JP1994-315457A (JP-H06-315457A) discloses a technique that coats a portion of an operation wire, which extends from a portion of the operation wire near a tip to a portion of the operation wire positioned in a tip portion body, with a coating member and water-tightly closes a gap between the tip portion of the coating member and the operation wire with an adhesive.

WO2016/027574A discloses an endoscope including an operation wire that includes a tip portion connected to a standing base and a base end portion connected to a standing operation unit and a stretchable coating member into which the tip portion side of the operation wire protruding from a housing part is inserted.

SUMMARY OF THE INVENTION

However, in the technique disclosed in JP1993-123288A (JP-H05-123288A), the operation wire is connected to the treatment tool-insertion channel and a standing base is not provided. For this reason, it is difficult to perform the same treatment tool operation as that of an endoscope including a standing base.

In the technique disclosed in JP1994-315457A (JP-H06-315457A), the operation wire and the coating member are fixed to each other by an adhesive. Accordingly, since the contaminated coating member is pulled into the tip portion body in a case in which the operation wire is pulled, there is a possibility that the inside of a packing in the tip portion body may also be contaminated.

In the technique disclosed in WO2016/027574A, there is a concern that the coating member may be damaged due to the contact between the outer periphery or the inner periphery of the coating member and other members.

The invention has been made in consideration of the above-mentioned circumstances, and an object of the invention is to provide an endoscope that can prevent the contamination of an operation wire and includes a standing base capable of preventing damage to an outer periphery or an inner periphery of a coating member.

An endoscope according to a first aspect comprises an insertion unit that includes a tip and a base end, a tip portion body that is provided on a tip side of the insertion unit, a standing base that is adapted to be rotatable in a receiving chamber provided in the tip portion body, an operation wire of which a tip side is connected to the standing base, an operation wire-guide passage that is provided in the tip portion body to guide the operation wire to be inserted into an internal space of the insertion unit to the standing base, and a stretchable coating member that covers the operation wire so as to extend in an extending direction of the operation wire and so as to allow the operation wire to be relatively movable over the entire region from a connection portion between the standing base and the operation wire to the operation wire-guide passage. A tip of the coating member and the standing base are liquid-tightly fixed to each other and a base end of the coating member and the operation wire-guide passage are liquid-tightly fixed to each other, and the coating member is disposed at a position where a moving path of the coating member caused by an operation of the standing base and a moving path of a treatment tool led from a treatment tool-guide passage provided in the tip portion body do not interfere with each other.

According to a second aspect, in the endoscope, the coating member is disposed at a position that is offset from the moving path of the treatment tool by a distance equal to or longer than a distance exceeding an increase in a diameter of the coating member in a case in which the coating member is contracted.

According to a third aspect, in the endoscope, the standing base is made to stand by an operation of the operation wire and pinches the treatment tool by the tip portion body and the standing base.

According to a fourth aspect, the endoscope further comprises a tip cap that is detachably mounted on the tip portion body. The tip cap includes a partition wall partitioning a first chamber in which the standing base is disposed and a second chamber in which the coating member is disposed, and the partition wall includes a slit communicating with the first chamber and the second chamber so that the coating member extending from the side of the standing base is movable with the rotation of the standing base.

According to a fifth aspect, in the endoscope, the coating member is in a contracted state or has a natural length in a first rotation range from a standing position in the entire rotation range of the standing base, and is stretched in a second rotation range in which the coating member is rotated to a falling position from the first rotation range.

According to a sixth aspect, in the endoscope, the first rotation range is a range of ½ to ⅔ of the entire rotation range from the standing position.

According to a seventh aspect, in the endoscope, the coating member has a bellows structure in which a large-diameter portion and a small-diameter portion are repeated in an axial direction.

According to an eighth aspect, the endoscope further comprises a tubular member that protrudes around a lead-out side of the operation wire-guide passage, and the base end of the coating member is liquid-tightly fixed to the tubular member.

According to a ninth aspect, in the endoscope, the tip of the coating member is closed and receives a tip of the operation wire.

An endoscope according to a tenth aspect comprises an insertion unit that includes a tip and a base end, a tip portion body that is provided on a tip side of the insertion unit, a standing base that is adapted to be rotatable in a receiving chamber provided in the tip portion body, an operation wire of which a tip side is connected to the standing base, an operation wire-guide passage that is provided in the tip portion body to guide the operation wire to be inserted into an internal space of the insertion unit to the standing base, and a stretchable coating member that covers the operation wire so as to extend in an extending direction of the operation wire and so as to allow the operation wire to be relatively movable over the entire region from a connection portion between the standing base and the operation wire to the operation wire-guide passage. A tip of the coating member and the standing base are liquid-tightly fixed to each other and a base end of the coating member and the operation wire-guide passage are liquid-tightly fixed to each other, and the coating member and the operation wire are spaced apart from each other in a state in which the coating member is contracted.

According to an eleventh aspect, in the endoscope, the standing base is made to stand by an operation of the operation wire, and pinches a treatment tool led from a treatment tool-guide passage by the tip portion body and the standing base.

According to a twelfth aspect, in the endoscope, the operation wire is inserted at a position offset from a center axis of the coating member in a radial direction.

According to a thirteenth aspect, in the endoscope, the standing base includes an operation wire-mounting hole, the operation wire-mounting hole of the standing base is formed of a cam groove in which the operation wire is movable, and the coating member and the operation wire are linearly reciprocated while the standing base is rotated between a standing position and a falling position.

According to a fourteenth aspect, in the endoscope, the coating member includes a coil spring and a resin member that covers the coil spring and protrudes to an outer periphery of the coil spring in a case in which the resin member is contracted.

An endoscope according to a fifteenth aspect comprises an insertion unit that includes a tip and a base end, a tip portion body that is provided on a tip side of the insertion unit, a standing base that is adapted to be rotatable in a receiving chamber provided in the tip portion body, an operation wire of which a tip side is connected to the standing base, an operation wire-guide passage that is provided in the tip portion body to guide the operation wire to be inserted into an internal space of the insertion unit to the standing base, and a stretchable coating member that covers the operation wire so as to extend in an extending direction of the operation wire and so as to allow the operation wire to be relatively movable over the entire region from a connection portion between the standing base and the operation wire to the operation wire-guide passage. A tip of the coating member and the standing base are liquid-tightly fixed to each other and a base end of the coating member and the operation wire-guide passage are liquid-tightly fixed to each other, the coating member is disposed at a position where a moving path of the coating member caused by an operation of the standing base and a moving path of a treatment tool led from a treatment tool-guide passage provided in the tip portion body do not interfere with each other, and the coating member and the operation wire are spaced apart from each other in a state in which the coating member is contracted.

According to the invention, in an endoscope including a standing base, the contamination of an operation wire can be prevented and damage to an outer periphery or an inner periphery of a coating member can be prevented.

DESCRIPTION OF THE PREFERRED EMBODIMENTS

Preferred embodiments of the invention will be described below with reference to the accompanying drawings. The invention will be described using the following preferred embodiments. The invention can be modified by many methods without departing from the scope of the invention, and embodiments other than this embodiment can be used. Accordingly, all modifications in the scope of the invention are included in claims.

Figure 1:
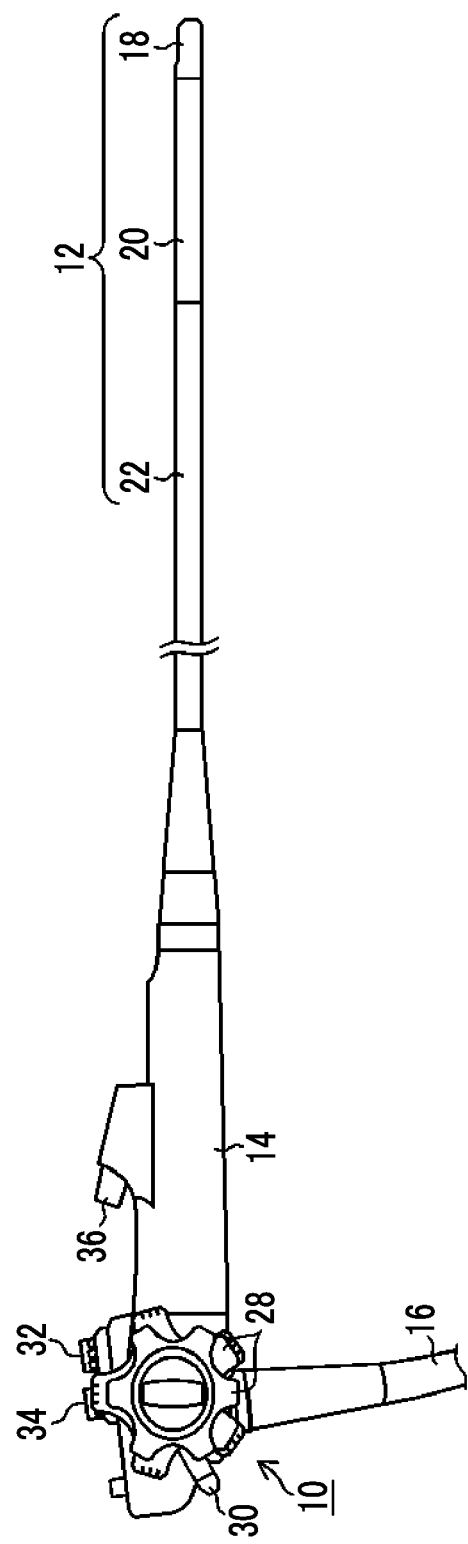
FIG. 1 is a side view showing the entire structure of an endoscope.

An endoscope according to an embodiment will be described below with reference to the accompanying drawings. FIG. 1 is a side view showing the entire structure of an endoscope 10 for side-viewing.

[Entire Structure of Endoscope]

The endoscope 10 includes an insertion unit 12 that is to be inserted into the body of a subject, and an operation unit 14 is connected to a base end side of the insertion unit 12. A universal cord 16 is connected to the operation unit 14, and the endoscope 10 is connected to a light source device, an image processing device, and an air/water supply device, which are not shown, through the universal cord 16.

<Entire Structure of Insertion Unit>

The insertion unit 12 includes a tip and a base end, and includes a tip portion 18, a bendable part 20, and a soft part 22 that are arranged from a tip side thereof toward the base end side thereof and are connected. A treatment tool-insertion channel 24 (see FIG. 2) that guides a treatment tool to the tip portion 18, an operation wire 26 (see FIG. 2) that changes the lead-out direction of the treatment tool led from the tip portion 18, a light guide (not shown) that guides illumination light supplied from the light source device to the tip portion 18, an air/water supply tube (not shown) that guides air and water supplied from the air/water supply device to the tip portion 18, and a signal cable (not shown) that transmits a signal sent from an imaging unit (not shown) disposed at the tip portion 18 are inserted into the insertion unit 12.

<Structure of Operation Unit>

Two angle knobs 28 that are used to bend the bendable part 20, an operation lever 30 that is used to change the lead-out direction of the treatment tool led from the tip portion 18 by pushing and pulling the operation wire 26 (see FIG. 2), an air/water supply button 32 that is used to eject air and water from an air/water supply nozzle 69 (see FIG. 2) provided at the tip portion 18, and a suction button 34 that is used to suck body fluid, such as blood, from a suction port (not shown) provided at the tip portion 18 are provided at predetermined positions on the operation unit 14. The operation lever 30 corresponds to a drive source that rotates a standing base to be described below.

Further, the operation unit 14 is provided with a treatment tool inlet 36 into which various treatment tools are introduced. A treatment tool introduced from the treatment tool inlet 36 is led from a treatment tool-guide passage 45 (see FIG. 2), which is provided in a tip portion body 40 of the tip portion 18, to the outside through the treatment tool-insertion channel 24 (see FIG. 2) inserted into the insertion unit 12. The treatment tool-guide passage 45 is formed of a through hole that is formed in the tip portion body 40.

<Structure of Bendable Part>

The bendable part 20 has a structure in which a plurality of angle rings (not shown) are connected to each other so as to be rotatable relative to each other. The outer periphery of the structure of the bendable part 20 is coated with a cylindrical net body knitted with metal wires and the outer peripheral surface of the net body is coated with an outer cover made of rubber, so that the bendable part 20 is formed. Further, a plurality of wires (not shown) are provided over the bendable part 20 from the two angle knobs 28 of the operation unit 14. Tips of these wires are fixed to the tip portion of the angle rings of the bendable part 20. Accordingly, these wires are pushed and pulled by the rotation of the two angle knobs 28, so that the bendable part 20 is bent up, down, left, and right.

<Structure of Soft Part>

The soft part 22 includes a spiral tube that is formed of an elastic thin strip-shaped plate that is made of metal and is spirally wound. The soft part 22 includes a cylindrical net body and an outer cover that are provided outside the spiral tube. The net body is knitted with coated metal wires, and the outer cover is coated on the outer peripheral surface of the net body and is made of a resin.

<Structure of Tip Portion>

Figure 2:
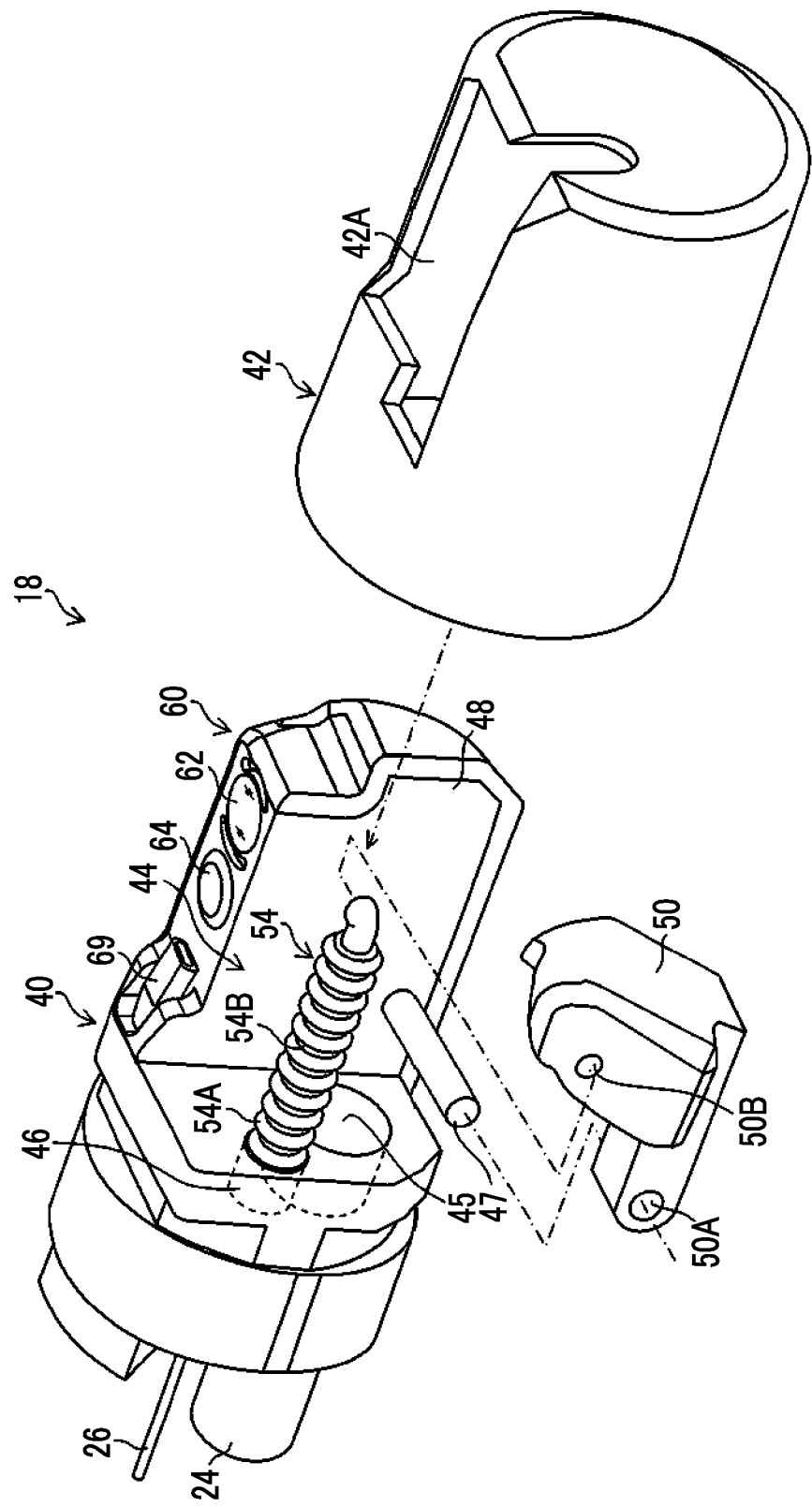
FIG. 2 is an exploded perspective view showing the structure of a tip portion of an insertion unit.

FIG. 2 is an exploded perspective view showing the structure of the tip portion 18. The tip portion 18 includes the tip portion body 40 and a tip cap 42 that is mounted on the tip portion body 40 and covers the tip portion body 40. The tip portion body 40 is provided on the tip side of the insertion unit 12. The tip portion body 40 is provided with a receiving chamber 44 that is a space for receiving a standing base 50. The tip cap 42 is detachably mounted on the tip portion body 40.

The treatment tool-guide passage 45, which communicates with the treatment tool-insertion channel 24, is formed in the tip portion body 40. In addition, an operation wire-guide passage 46 into which the operation wire 26 is to be inserted is formed in the tip portion body 40, and the operation wire-guide passage 46 guides the operation wire 26, which is inserted into the internal space of the insertion unit 12, to the standing base 50. It is preferable that tip portion body 40 is made of a metal material having corrosion resistance, such as stainless steel. The operation wire-guide passage 46 is formed of a through hole that is formed in the tip portion body 40.

The tip cap 42 has substantially the shape of a cylinder which is closed on the tip side thereof, and includes a substantially rectangular opening window 42A that is formed on a part of the outer peripheral surface of the tip cap 42. The tip cap 42 is made of an elastic material, for example, fluororubber or silicon rubber. The tip cap 42 includes an engagement portion (not shown) that is formed on the base end side of the tip cap 42 and is engaged with a groove (not shown) formed on the tip portion body 40, and is detachably mounted on the tip portion body 40 through engagement between the engagement portion and the groove. In a case in which the tip cap 42 is mounted on the tip portion body 40, the treatment tool-guide passage 45 communicates with the outside air through the receiving chamber 44 and the opening window 42A.

The receiving chamber 44 and the treatment tool-insertion channel 24 communicate with each other through the treatment tool-guide passage 45. A base end of the treatment tool-insertion channel 24 is inserted into the insertion unit 12, and is connected to the treatment tool inlet 36 of the operation unit 14. A treatment tool is introduced into the base end of the treatment tool-insertion channel 24 from the treatment tool inlet 36, and is guided to the receiving chamber 44 from the tip of the treatment tool-insertion channel 24 through the treatment tool-insertion channel 24.

The standing base 50 is housed in the receiving chamber 44. The standing base 50 is a treatment tool-standing base that is used to change the direction of the treatment tool led from the treatment tool-guide passage 45 to the outside. A shaft portion 47, which protrudes into the receiving chamber 44, is provided on a partition wall 48 of the tip portion body 40. The standing base 50 includes a through hole 50A, and the shaft portion 47 is inserted into the through hole 50A of the standing base 50. The standing base 50 is adapted to be rotatable about the shaft portion 47.

As shown in FIG. 2, the operation wire 26 is guided to the standing base 50 by the operation wire-guide passage 46 of the tip portion body 40 and the tip side of the operation wire 26 is connected to the standing base 50. For example, the tip of the operation wire 26 is inserted into a hole 50B that is an operation wire-mounting hole formed in the standing base 50 and a connection portion 52 (see FIG. 3) between the operation wire 26 and the standing base 50 is liquid-tightly fixed by an adhesive or the like (not shown), so that the operation wire 26 and the standing base 50 can be connected to each other.

In a case in which the connection portion 52 between the operation wire 26 and the standing base 50 is fixed by an adhesive or the like, the posture of the standing base 50 is changed without the rotation of the operation wire 26. Since the connection portion 52 is fixed by an adhesive or the like, washability can be improved.

The operation wire 26 is inserted into the internal space of the insertion unit 12 by the operation wire-guide passage 46, and a base end side of the operation wire 26 is connected to the operation lever 30 of the operation unit 14. An operation for pushing and pulling the operation wire 26 is performed by the operation lever 30 (see FIG. 1). The standing base 50 is rotated about the shaft portion 47 by the operation for pushing and pulling the operation wire 26. The posture of the standing base 50 is changed between a standing position and a falling position by the rotation of the standing base 50.

As shown in FIG. 2, an optical system-receiving chamber 60 is provided on the side of the partition wall 48 opposite to the receiving chamber 44. The airtightness of the optical system-receiving chamber 60 is kept in a case in which the tip portion body 40 is covered with a protective plate (not shown).

An illumination window 62 and an observation window 64 are provided at an upper portion of the optical system-receiving chamber 60 so as to be adjacent to each other. The tip portion body 40 is provided with the air/water supply nozzle 69 that is directed toward the observation window 64. The air/water supply nozzle 69 is connected to the air/water supply device through an air/water supply tube (not shown) that is inserted into the insertion unit 12. Compressed air or water is ejected to the observation window 64 from the air/water supply nozzle 69 by the operation of the air/water supply button 32 of the operation unit 14 shown in FIG. 1, so that the observation window 64 is washed.

An illumination unit and an imaging unit (not shown) are received in the optical system-receiving chamber 60. The illumination unit includes an illumination lens that is installed inside the illumination window 62 and a light guide that is disposed so that the tip of the light guide faces the illumination lens. The light guide is inserted into the insertion unit 12 of the endoscope 10, and a base end of the light guide is connected to the light source device. Accordingly, light emitted from the light source device is transmitted through the light guide, and is emitted to the outside from the illumination window 62.

The imaging unit includes an imaging optical system that is disposed inside the observation window 64 and a CMOS (complementary metal oxide semiconductor) or CCD (charge coupled device) type imaging element. The imaging element is connected to the above-mentioned image processing device through the signal cable that is inserted into the insertion unit 12 and the universal cord 16. After an imaging signal of a subject image, which is obtained by the imaging unit, is output to the above-mentioned image processing device through the signal cable and is subjected to image processing, the imaging signal is displayed on a monitor, which is connected to the image processing device, as the subject image.

In this embodiment, the operation wire 26 is covered with a stretchable coating member 54 over the entire region from the connection portion 52 (see FIG. 3) between the standing base 50 and the operation wire 26 to the operation wire-guide passage 46. The coating member 54 extends in the extending direction of the operation wire 26. The coating member 54 and the operation wire 26 are adapted to be movable relative to each other. In addition, the tip of the coating member 54 and the standing base 50 are liquid-tightly fixed to each other, and the base end of the coating member 54 and the operation wire-guide passage 46 are liquid-tightly fixed to each other.

Since the coating member 54 covers the operation wire 26 over the entire region from the connection portion 52 to the operation wire-guide passage 46, the operation wire 26 is not exposed over the entire region. In addition, since the coating member 54 and the standing base 50 are liquid-tightly fixed to each other and the coating member 54 and the operation wire-guide passage 46 are liquid-tightly fixed to each other, the contamination of the operation wire 26 inserted into the coating member 54 can be prevented.

"Liquid-tightly" means a state in which liquid does not permeate the inside of the coating member 54 from a boundary between the coating member 54 and the standing base 50 and a boundary between the coating member 54 and the tip portion body 40 formed on the operation wire-guide passage 46. Specifically, "liquid-tightly" is about IPX-7 that is the indicator of waterproof performance, and means a watertight state in which water does not permeate the inside of the coating member 54 even though the coating member 54 is temporarily submerged under the condition of a certain water pressure.

Further, since the coating member 54 is exposed even in a case in which the coating member 54 is contaminated, the coating member 54 can be reliably washed.

Since the coating member 54 and the operation wire 26 are not closely attached to each other and are not fixed to each other, the coating member 54 and the operation wire 26 are movable relative to each other during an operation for pushing and pulling the operation wire 26. Accordingly, even in a case in which the operation wire 26 is pulled to the side of the operation unit 14 by the operation lever 30, the coating member 54 is not pulled into the tip portion body 40. The contamination of the inside of the tip portion body 40, which is caused by the coating member 54, can be prevented. Since the coating member 54 is stretchable, the coating member 54 can follow the change of the posture of the standing base 50. Accordingly, the coating member 54 can prevent the exposure of the operation wire 26.

In this embodiment, the coating member 54 has a bellows structure in which a large-diameter portion 54A and a small-diameter portion 54B are repeated in an axial direction that is the extending direction of the coating member 54 as shown in FIG. 2. Since the coating member 54 has the bellows structure, the coating member 54 has stretchability.

It is preferable that the outer diameter of the large-diameter portion 54A of the coating member 54 having the bellows structure is 2.5 mm or less in a case in which the coating member 54 is most contracted. Since the outer diameter of the large-diameter portion 54A is set to 2.5 mm or less, it is possible to avoid an increase in the size of the tip portion 18.

Further, it is preferable that the inner diameter of the small-diameter portion 54B of the coating member 54 having the bellows structure is 0.7 mm or more in a case in which the coating member 54 is most stretched. It is preferable that the diameter of the operation wire 26 is about 0.6 mm and the inner diameter of the small-diameter portion 54B is set to be larger than the diameter of the operation wire 26. Furthermore, it is preferable that the coating member 54 is made of a material having chemical resistance and liquid-tightness. It is preferable that PTFE (polytetrafluoroethylene), PFA (tetrafluoroethylene-perfluoroalkyl vinyl ether copolymer), fluororubber, silicon rubber, and EPDM (ethylene propylene diene monomer), and the like are used as the material of the coating member 54.

The coating member 54 having the bellows structure has been exemplified as the stretchable coating member 54 in this embodiment, but the structure of the coating member 54 is not limited to the bellows structure. A stretchable cylindrical rubber tube can be used as the coating member instead of the coating member 54 having the bellows structure. Even though a coating member formed of a rubber tube is used, the coating member can cover the operation wire 26 over the entire region from the connection portion 52 to the operation wire-guide passage 46. Further, the coating member 54 can be adapted so that the coating member 54 and the operation wire 26 are movable relative to each other in the extending direction of the operation wire 26. The coating member 54 and the standing base 50 are liquid-tightly fixed to each other, and the coating member 54 and the operation wire-guide passage 46 are liquid-tightly fixed to each other.

Figure 3:
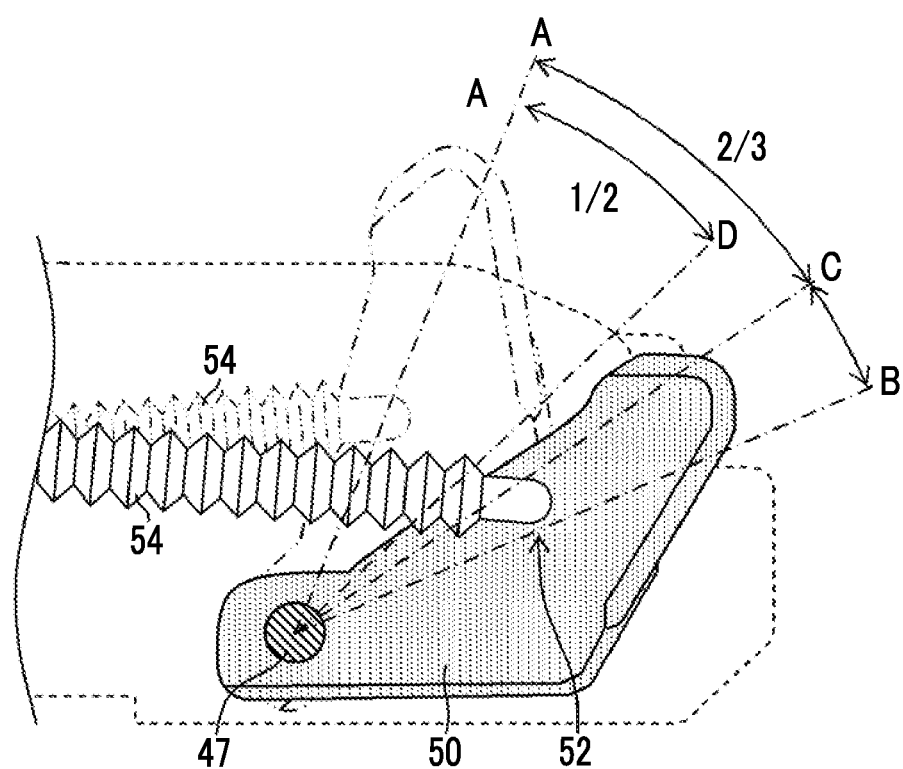
FIG. 3 is a side view showing the rotation range of a standing base.

Next, a relationship between the rotation range of the standing base and the coating member will be described with reference to FIG. 3. FIG. 3 is a side view showing the rotation range of the standing base 50. As shown in FIG. 3, the standing base 50 can change the posture thereof in the entire rotation range between a standing position A and a falling position B.

It is preferable that the coating member 54 is in a contracted state or has a natural length in a first rotation range between the standing position A of the standing base 50 and a first position C. It is preferable that the coating member 54 is stretched in a second rotation range (C-B) between the first position C and a falling position B. Here, the first position C is a position at which the standing base 50 has been rotated toward the side of the falling position B from the standing position A, and a second position D is a position at which the standing base 50 has been rotated toward the side of the standing position A from the first position C.

It is preferable that the coating member 54 has a natural length in a range of ½ to ⅔ of the entire rotation range from the standing position A of the standing base 50 in the first rotation range (A-C). That is, it is preferable that the coating member 54 has a natural length between the second position D and the first position C. A treatment tool (not shown) is positioned in the field of view of the endoscope in a range of ⅔ or less of the entire rotation range from the standing position A of the standing base 50. Further, a range in which the standing base 50 is operated by the operation wire 26 is a range of ½ or more of the entire rotation range from the standing position A of the standing base 50. Accordingly, in a case in which the coating member 54 has a natural length in a range of ½ to ⅔ of the entire rotation range from the standing position A, the stretchability of the coating member 54 can be ensured between the standing position A and the falling position B. Therefore, it is preferable that the coating member 54 has a natural length in a range of ½ to ⅔ of the entire rotation range from the standing position A.

A natural length means a length in a state in which a tensile force or a compressive force is not applied to the coating member 54. Stretching means a state in which a tensile force is applied to the coating member 54 so that the length of the coating member 54 is longer than a natural length, and contraction means a state in which a compressive force is applied to the coating member 54 so that the length of the coating member 54 is shorter than a natural length.

Figure 4:
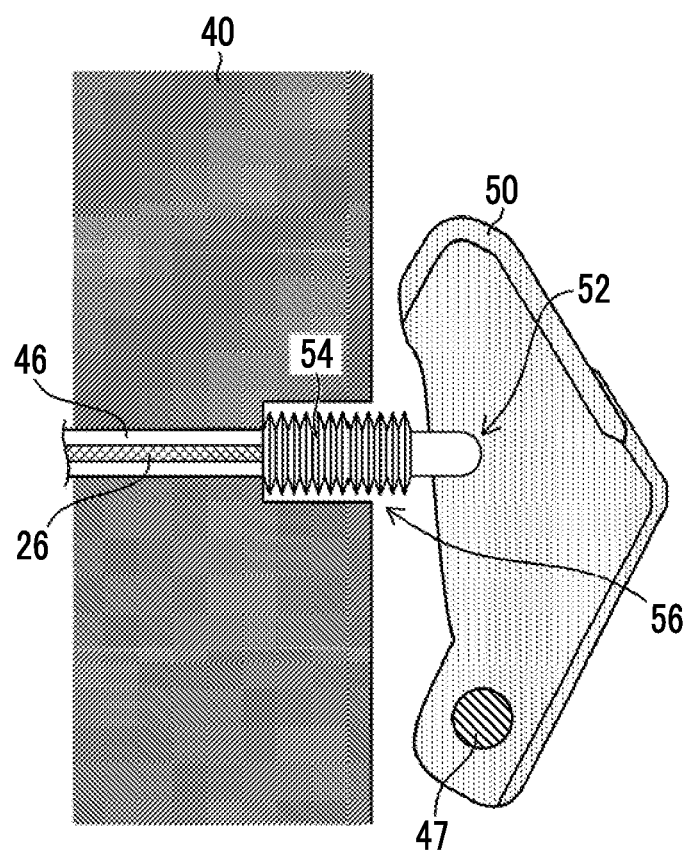
FIG. 4 is an enlarged view of main parts of a tip portion body.

Next, a preferred method of fixing the coating member to the operation wire-guide passage will be described. FIG. 4 is an enlarged view of main parts of the tip portion body. As shown in FIG. 4, the standing base 50 is positioned at the standing position. At the standing position of the standing base 50, the operation wire 26 is in a state in which the operation wire 26 is most pulled by the operation lever 30. Since the coating member 54 is liquid-tightly fixed to the tip portion body 40 on the side of the operation wire-guide passage 46 from which the operation wire 26 is led, the coating member 54 is in a state in which the coating member 54 is most contracted by the operation of the operation wire 26.

In a case in which the coating member 54 having stretchability is contracted, the coating member 54 expands in a radial direction due to the contraction deformation thereof. Further, there is a concern that the coating member 54 may hinder the operation of the operation wire 26 in a case in which the coating member 54 reaches the limit of contraction. In the embodiment shown in FIG. 4, a recessed portion 56, which receives the coating member 54 to be contracted, is formed in the tip portion body 40 on the lead-out side of the operation wire-guide passage 46. The shape change of the coating member 54, which is caused by the contraction, can be allowed by the recessed portion 56.

Figure 5:
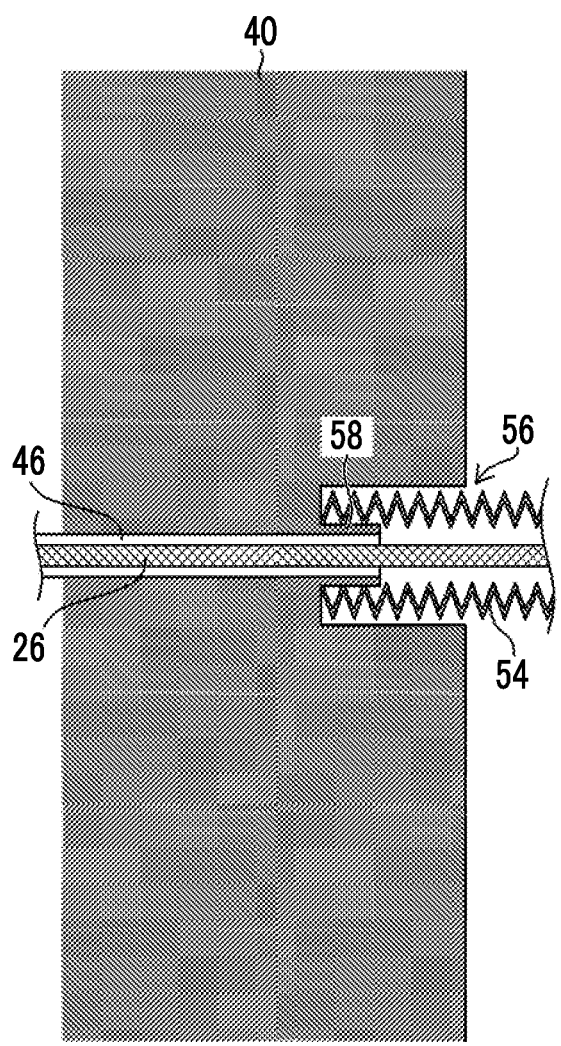
FIG. 5 is an enlarged view of main parts of the tip portion body.

Next, another preferred method of fixing the coating member to the operation wire-guide passage will be described. FIG. 5 is an enlarged view of main parts of the tip portion body. The same components as the components of FIG. 4 may be denoted by the same reference numerals as the reference numerals of FIG. 4, and the description thereof may be omitted.

As shown in FIG. 5, a recessed portion 56 is formed in the tip portion body 40 on the lead-out side of the operation wire-guide passage 46. In addition, a tubular member 58, which protrudes toward the standing base 50 (not shown), is provided around the lead-out side of the operation wire-guide passage 46 in the recessed portion 56. It is preferable that the tubular member 58 and the coating member 54 are liquid-tightly fixed to each other by an adhesive or the like. Since the outer peripheral surface of the tubular member 58 and the coating member 54 are fixed to each other, the coating member 54 can be more firmly and liquid-tightly fixed to the operation wire-guide passage 46.

In FIG. 5, the tubular member 58 is formed in the recessed portion 56. The invention is not limited thereto, and the tubular member 58 can be provided on a portion of the tip portion body 40 in which the recessed portion 56 is not formed and the tubular member 58 and the coating member 54 can be liquid-tightly fixed to each other.

The tubular member 58 is not limited to a cylindrical shape, and can be formed in the shape of a cylinder that includes slits extending in a protruding direction.

Figure 6:
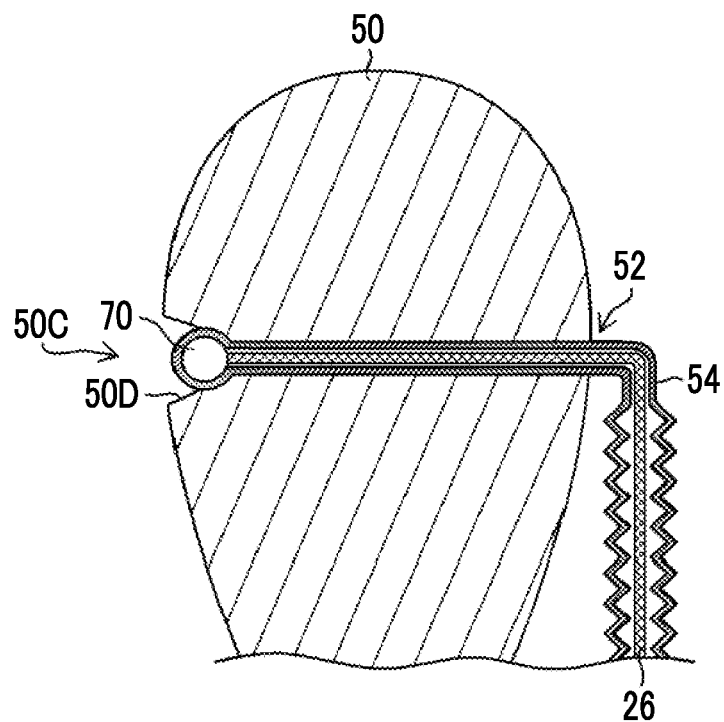
FIG. 6 is a cross-sectional view of main parts of the standing base.

Next, a preferred method of fixing the standing base to the coating member will be described. FIG. 6 is a cross-sectional view of main parts of the standing base. As shown in FIG. 6, a substantially spherical locking portion 70, which has a diameter larger than the diameter of the operation wire 26, is provided at the tip of the operation wire 26. Since the tip of the coating member 54 is closed in this embodiment, the tip (here, the locking portion 70) of the operation wire 26 can be received in the coating member 54.

Since the tip of the coating member 54 is closed, the operation wire 26 can be protected from contamination over the entire region from the operation wire-guide passage 46 to the tip of the operation wire 26 by the coating member 54. It is preferable that the coating member 54 is formed of a heat-shrinkable tube. The tip of the operation wire 26 can be easily coated with the heat-shrinkable tube. For example, polyolefin and a fluorine resin can be used for the heat-shrinkable tube.

A through hole 50C is formed in the standing base 50 as the operation wire-mounting hole, and the operation wire 26 coated with the coating member 54 is inserted into the through hole 50C. Further, a tapered surface 50D, which expands toward the tip, is formed on the tip side of the through hole 50C of the standing base 50. The diameter of the tapered surface 50D is larger than the diameter of the locking portion 70 on the tip side, and is smaller than the diameter of the locking portion 70 on the base end side. Since the locking portion 70 is locked by the tapered surface 50D of the through hole 50C as shown in FIG. 6, the separation of the operation wire 26 from the standing base 50 can be suppressed.

The through hole 50C of the standing base 50 and the outer periphery of the coating member 54 may be fixed to each other by an adhesive or the like, and may not be fixed to each other. Washability is improved in a case in which the through hole 50C of the standing base 50 and the outer periphery of the coating member 54 are fixed to each other. Further, since the standing base 50 and the coating member 54 can be rotated relative to each other in a case in which the through hole 50C of the standing base 50 and the outer periphery of the coating member 54 are not fixed to each other, the standing base 50 can be operated to stand smoothly.

During the assembly, the operation wire 26 is coated with the coating member 54 and the operation wire 26 can be inserted into the through hole 50C of the standing base 50 from the side of the tapered surface 50D in a state in which the tip of the operation wire 26 is closed.

Figure 7:
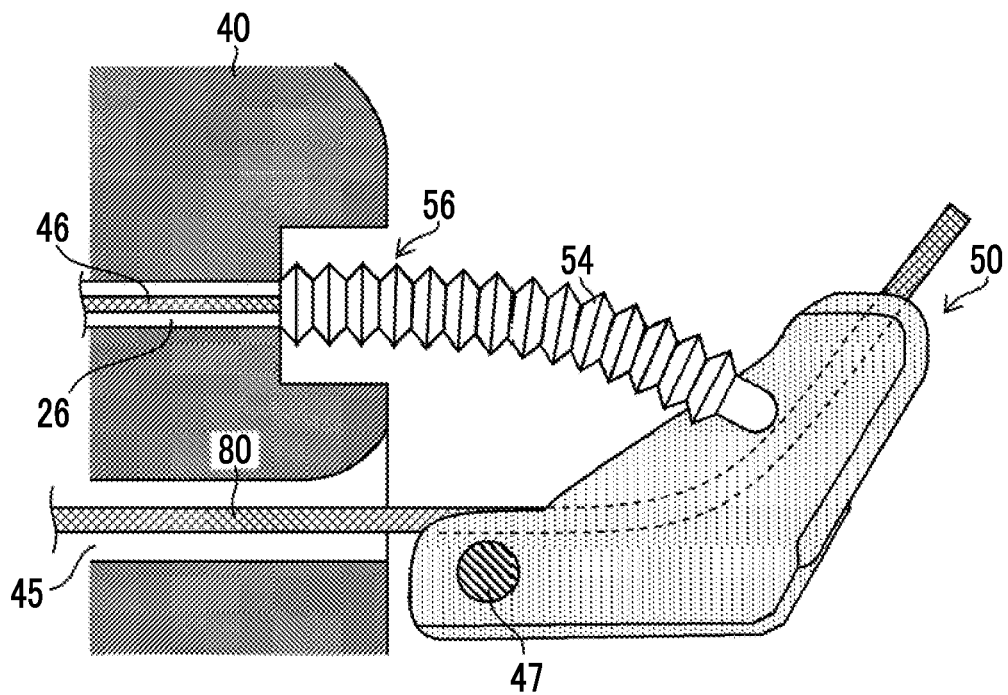
FIG. 7 is a side view of the standing base at a falling position.

Next, a relative positional relationship between a coating member, a standing base, and a treatment tool, which can prevent damage to the outer periphery of the coating member, will be described with reference to FIGS. 7 to 10. FIG. 7 is a side view of the standing base at a falling position, FIG. 8 is a plan view of the standing base at the falling position, and FIG. 9 is a side view of the standing base at a standing position, and FIG. 10 is a plan view of the standing base at the standing position.

Figure 8:
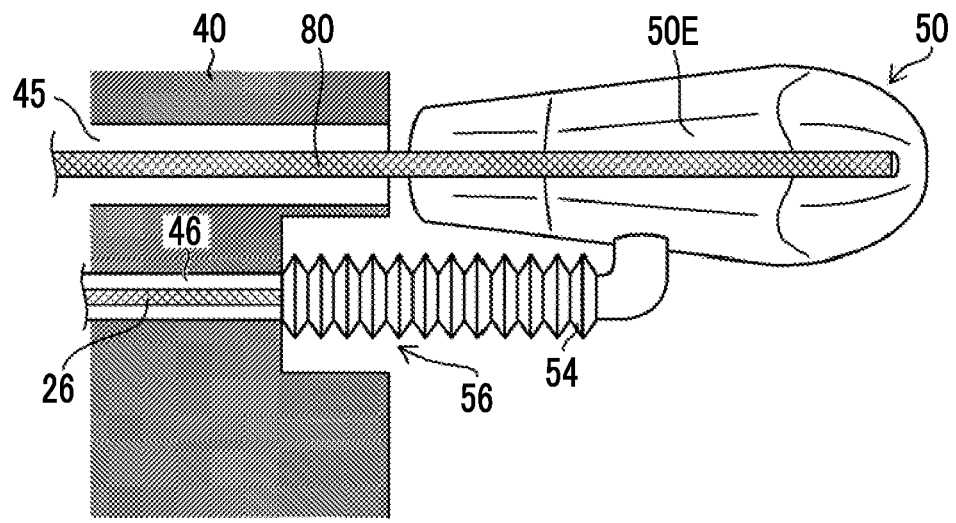
FIG. 8 is a plan view of the standing base at the falling position.

As shown in FIGS. 7 and 8, the treatment tool 80 is guided to the standing base 50 in an axial direction of the insertion unit 12 (not shown) by the treatment tool-guide passage 45 formed in the tip portion body 40. As shown in FIG. 8, the standing base 50 includes a guide surface 50E. During the insertion of the treatment tool 80, the treatment tool 80 is guided on the standing base 50 by the guide surface 50E. Then, in a case in which the standing base 50 is rotated to the standing position, the treatment tool 80 is led from the opening window 42A (not shown) of the tip cap 42 to the outside of the tip portion 18 while the vibration of the treatment tool 80 caused by the change of the posture of the treatment tool 80 is suppressed by the guide surface 50E. For example, a guide wire, a tube for cannulation, and the like can be used as the treatment tool 80.

The coating member 54 is in a state in which the coating member 54 is most stretched in a case in which the standing base 50 is at the falling position. The coating member 54 of this embodiment has a bellows structure. There is a case in which the coating member 54 contracts inward in a radial direction due to the stretching deformation of the coating member 54. As shown in FIG. 8, in this embodiment, the coating member 54, the standing base 50, and the treatment tool 80 are disposed at positions where the moving path of the coating member 54 caused by the operation of the standing base 50 (the rotation of the standing base 50 to the falling position) and the moving path of the treatment tool 80 led from the treatment tool-guide passage 45 formed in the tip portion body 40 do not interfere with each other. Since the treatment tool 80 and the coating member 54 are not in contact with each other, it is possible to prevent the outer periphery of the coating member 54 from being damaged.

Figure 9:
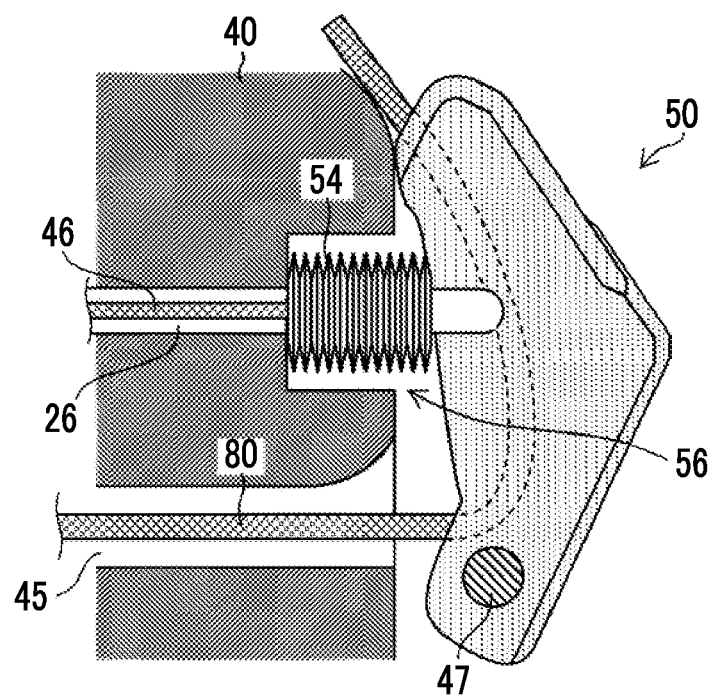
FIG. 9 is a side view of the standing base at a standing position.
Figure 10:
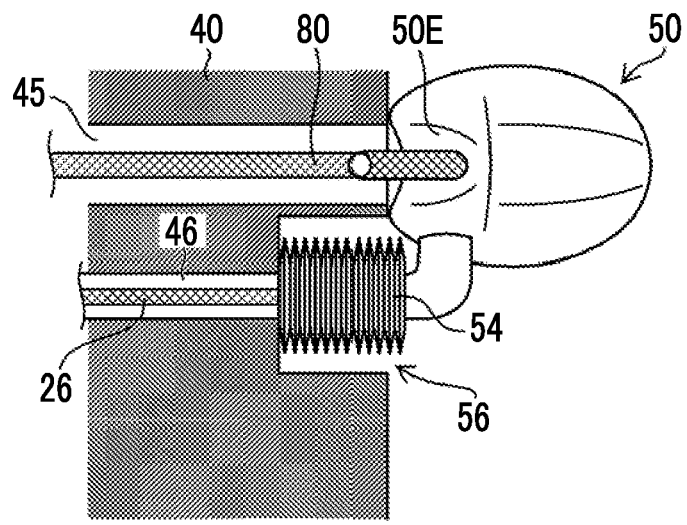
FIG. 10 is a plan view of the standing base at the standing position.

As shown in FIGS. 9 and 10, the lead-out direction of the treatment tool 80 is controlled by the guide surface 50E of the standing base 50. The coating member 54 is in a state in which the coating member 54 is most contracted in a case in which the standing base 50 is at the standing position. There is a case in which the coating member 54 expands outward in the radial direction due to the contraction deformation of the coating member 54.

As shown in FIG. 10, in this embodiment, the coating member 54, the standing base 50, and the treatment tool 80 are disposed at positions where the moving path of the coating member 54 caused by the operation of the standing base 50 (the rotation of the standing base 50 to the standing position) and the moving path of the treatment tool 80 led from the treatment tool-guide passage 45 formed in the tip portion body 40 do not interfere with each other. Since the treatment tool 80 and the coating member 54 are not in contact with each other, it is possible to prevent the outer periphery of the coating member 54 from being damaged.

That is, since the coating member 54 is disposed at a position where the moving path of the coating member 54 and the moving path of the treatment tool do not interfere with each other not only in a case in which the coating member 54 is deformed so as to be stretched due to the operation of the standing base 50 but also in a case in which the coating member 54 is deformed so as to be contracted, it is possible to prevent the outer periphery of the coating member 54 from being damaged.

Since the coating member 54 is disposed at the above-mentioned position, the lead-out direction of the treatment tool 80 is not hindered by the coating member 54 while the standing base 50 is rotated to the standing position from the falling position. That is, since the treatment tool 80 and the coating member 54 are not in contact with each other, it is possible to prevent the lead-out direction of the treatment tool 80 from being changed to an unintended direction.

Particularly, as shown in FIG. 10, in this embodiment, the coating member 54 is disposed at a position that is offset so as to be spaced apart from the moving path of the treatment tool 80 in a direction perpendicular to the moving path of the treatment tool 80 in plan view by a distance equal to or longer than a distance exceeding an increase in the diameter of the coating member 54 in a case in which the coating member 54 is contracted. That is, this means that the coating member 54 is spaced apart from the moving path to a position where the coating member 54 does not obstruct the moving path of the treatment tool 80 even though the diameter of the coating member 54 is increased in a case in which the coating member 54 is contracted.

As a result, since the standing base 50 can be made to stand by the operation of the operation wire 26 until the standing base 50 comes into contact with the tip portion body 40 as shown in FIG. 9, the treatment tool 80 can be pinched by the tip portion body 40 and the standing base 50. The treatment tool 80 can be locked by the tip portion body 40 and the standing base 50. Particularly, the locking of the treatment tool 80 is required in an examination or a treatment using a duodenoscope.

Further, in this embodiment, the operation wire-guide passage 46 is disposed substantially at the center position of the recessed portion 56. Even in a case in which the diameter of the coating member 54 is increased due to the contraction of the coating member 54, an increase in the diameter of the coating member 54 can be allowed by the recessed portion 56.

Figure 11:
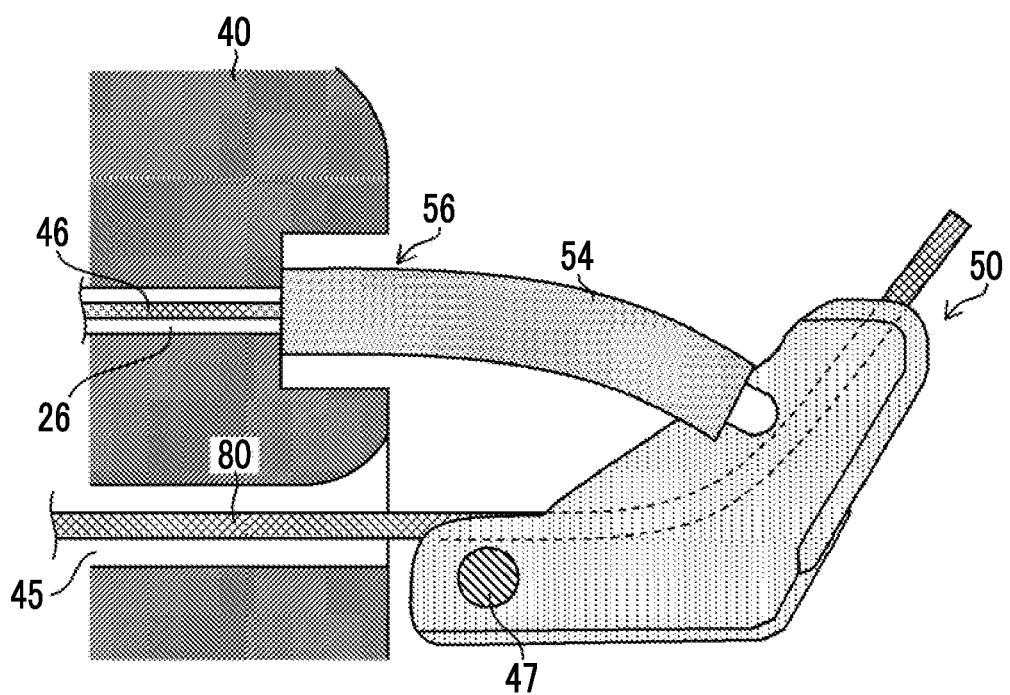
FIG. 11 is a side view of the standing base at the falling position.
Figure 12:
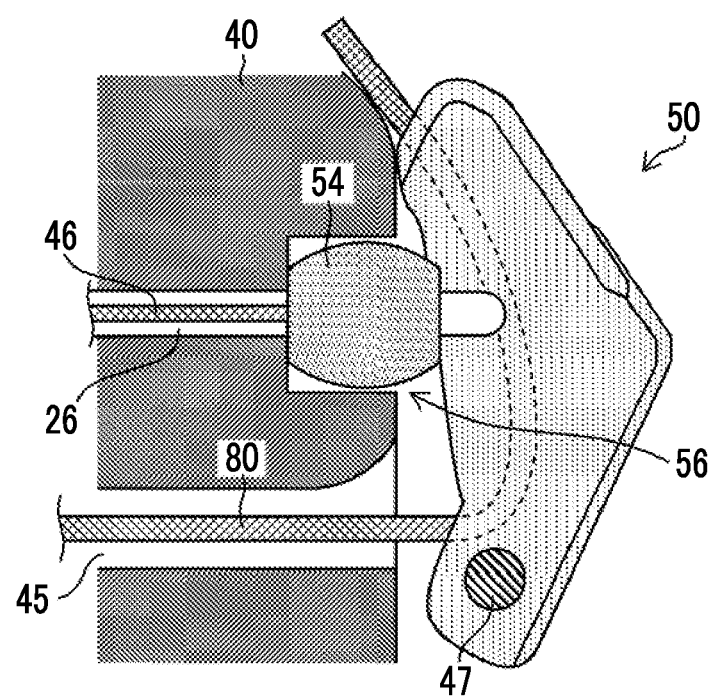
FIG. 12 is a side view of the standing base at the standing position.

Next, a case in which a coating member different from the coating member of FIGS. 7 to 10 is used will be described with reference to FIGS. 11 and 12. A coating member 54 of FIGS. 11 and 12 does not have a bellows structure and has a cylindrical shape in the case of a natural length. FIG. 11 is a side view of the standing base at the falling position, and FIG. 12 is a side view of the standing base at the standing position. The same components of the embodiment of FIGS. 11 and 12 as the components of the embodiment of FIGS. 7 to 10 may be denoted by the same reference numerals as the reference numerals of the embodiment of FIGS. 7 to 10, and the description thereof may be omitted.

The coating member 54 is in a state in which the coating member 54 is most stretched in a case in which the standing base 50 is at the falling position as shown in FIG. 11. Even in this embodiment, the coating member 54, the standing base 50, and the treatment tool 80 are disposed at positions where the moving path of the coating member 54 caused by the operation of the standing base 50 (the rotation of the standing base 50 to the falling position) and the moving path of the treatment tool 80 led from the treatment tool-guide passage 45 formed in the tip portion body 40 do not interfere with each other. Since the treatment tool 80 and the coating member 54 are not in contact with each other, it is possible to prevent the outer periphery of the coating member 54 from being damaged.

The coating member 54 is in a state in which the coating member 54 is most contracted in a case in which the standing base 50 is at the standing position as shown in FIG. 12. Particularly, there is a case in which the coating member 54 expands outward in the radial direction in comparison with the case of a natural length due to the contraction deformation of the cylindrical coating member 54. Even in this embodiment, the coating member 54, the standing base 50, and the treatment tool 80 are disposed at positions where the moving path of the coating member 54 caused by the operation of the standing base 50 (the rotation of the standing base 50 to the falling position) and the moving path of the treatment tool 80 led from the treatment tool-guide passage 45 formed in the tip portion body 40 do not interfere with each other. Since the treatment tool 80 and the coating member 54 are not in contact with each other even in a case in which the coating member 54 is contracted, it is possible to prevent the outer periphery of the coating member 54 from being damaged.

As a result, since the standing base 50 can be made to stand by the operation of the operation wire 26 until the standing base 50 comes into contact with the tip portion body 40 even in a case in which the cylindrical coating member 54 is used as shown in FIG. 12, the treatment tool 80 can be pinched by the tip portion body 40 and the standing base 50.

Further, in this embodiment, the operation wire-guide passage 46 is disposed substantially at the center position of the recessed portion 56. Even in a case in which the diameter of the coating member 54 is increased due to the contraction of the coating member 54, an increase in the diameter of the coating member 54 can be allowed by the recessed portion 56.

Figure 13:
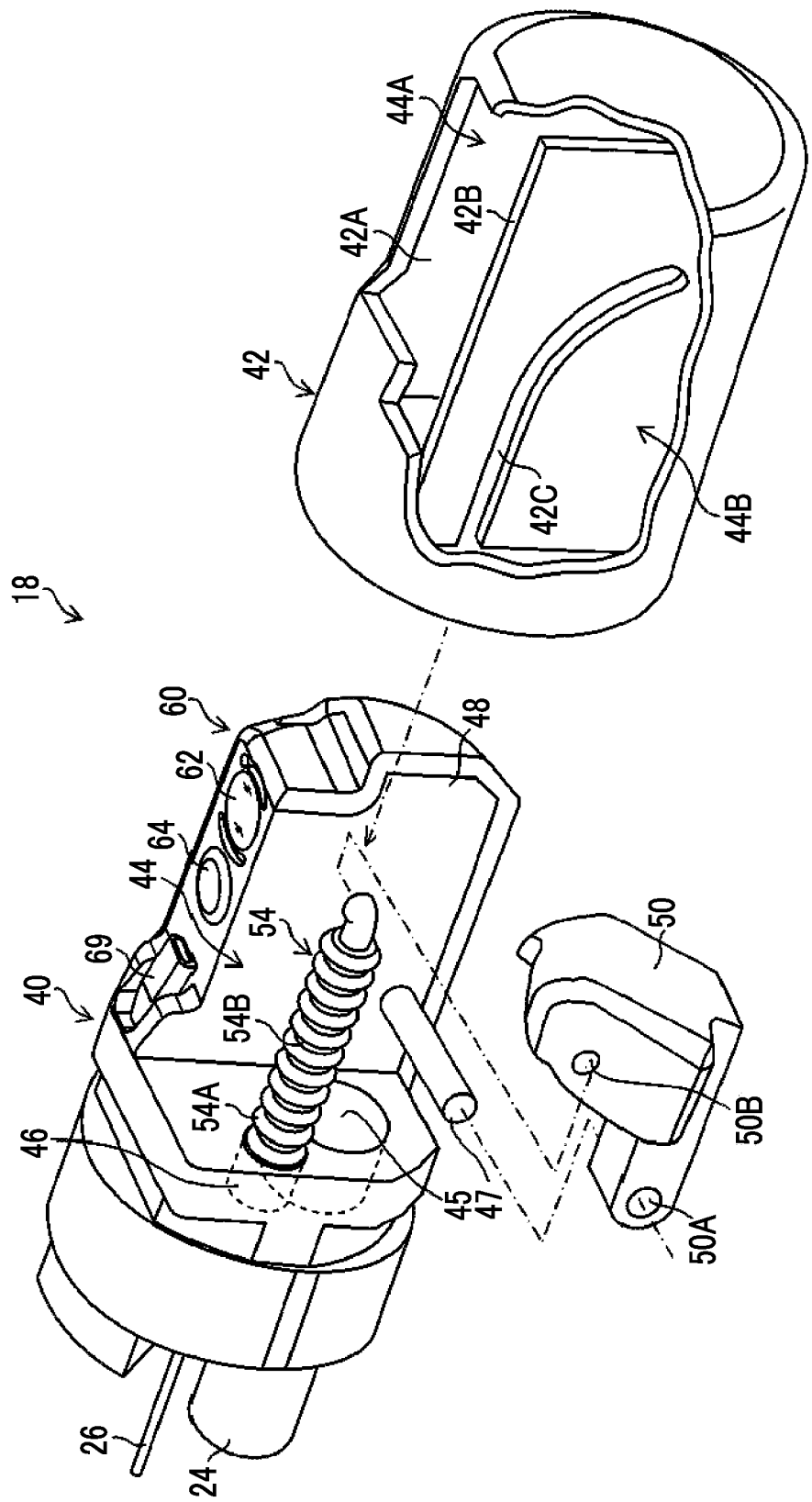
FIG. 13 is an exploded perspective view showing the structure of a tip portion of an insertion unit.

Next, another embodiment in which it is possible to prevent a coating member from obstructing the moving path of a treatment tool and damage to the outer periphery of the coating member can be prevented will be described with reference to FIG. 13. FIG. 13 is an exploded perspective view showing the structure of a tip portion of an insertion unit. The same components as the components of FIG. 2 may be denoted by the same reference numerals as the reference numerals of FIG. 2, and the description thereof may be omitted.

The tip cap 42 is detachably mounted on the tip portion body 40. The tip cap 42 is provided with a partition wall 42B including a slit 42C. In a case in which the tip cap 42 is mounted on the tip portion body 40, the partition wall 42B can partition the receiving chamber 44 into a first chamber 44A in which the standing base 50 is disposed and a second chamber 44B in which the coating member 54 is disposed.

The slit 42C communicates with the first chamber 44A and the second chamber 44B. A portion of the slit 42C corresponding to the base end side of the tip cap 42 is opened, and a portion of the slit 42C corresponding to the tip side of the tip cap 42 is closed. In a case in which the tip cap 42 is mounted on the tip portion body 40, the coating member 54 extending from the side of the standing base 50 is received in the slit 42C.

Since the slit 42C is formed according to the coating member 54, the coating member 54 is movable along the slit 42C with the rotation of the standing base 50. That is, the partition wall 42B including the slit 42C can allow the movement of the coating member 54.

Since the tip cap 42 is provided with the partition wall 42B, it is possible to prevent the coating member 54 from obstructing the moving path of the treatment tool 80 (not shown). The slit 42C has communicated with the first chamber 44A and the second chamber 44B, but the width of the opening of the slit 42C is not large. Accordingly, it is presumed that the entire coating member 54 does not pass through the slit 42C and does not obstruct the moving path of the treatment tool 80. It is preferable that the partition wall 42B is close to the standing base 50.

Since the contact between the treatment tool 80 and the coating member 54 can be avoided by the partition wall 42B, damage to the outer periphery of the coating member 54 can be prevented. Further, it is possible to prevent the lead-out direction of the treatment tool 80 from being changed to an unintended direction.

Next, a positional relationship between a coating member and an operation wire, which can prevent damage to the inner periphery of the coating member, will be described with reference to FIGS. 14 to 18. As described above, the operation wire 26 is coated with the coating member 54 and the operation wire 26 and the coating member 54 are adapted to be movable relative to each other. It is preferable that the operation wire 26 and the coating member 54 are not in contact with each other in a case in which the operation wire 26 and the coating member 54 are moved relative to each other with the operation of the standing base 50. There is a concern that the inner periphery of the coating member 54 may be damaged by the operation wire 26 in a case in which the operation wire 26 and the coating member 54 are in contact with each other. In this embodiment, the coating member 54 and the operation wire 26 are spaced apart from each other in a state in which the coating member 54 is contracted. Since the contact between the coating member 54 and the operation wire 26 can be avoided, damage to the inner periphery of the coating member 54 can be prevented.

Figure 14:
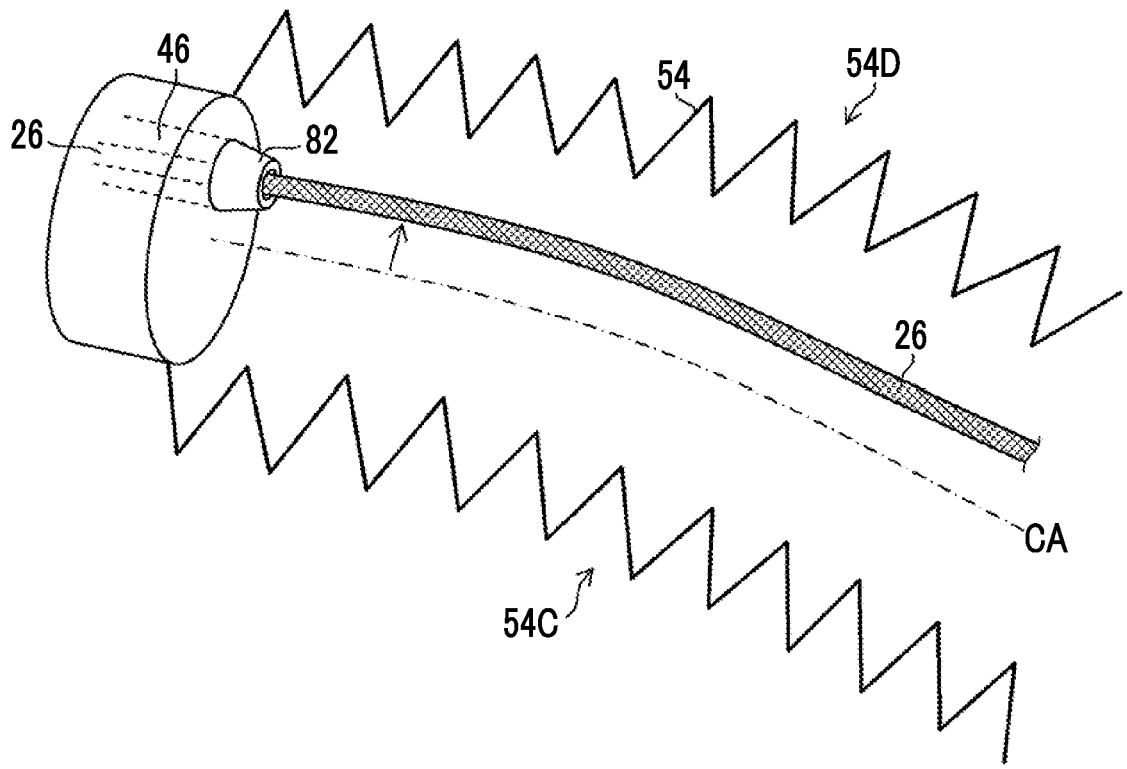
FIG. 14 is a view showing a positional relationship between an operation wire and a coating member.

FIG. 14 is a view showing a positional relationship between an operation wire and a coating member that can prevent damage to the inner periphery of the coating member. The coating member 54 is stretchably deformed so as to follow the standing base 50 as shown in FIG. 14 in a case in which the standing base 50 (not shown) is rotated to the falling position from the standing position. The coating member 54, which is fixed to the operation wire-guide passage 46, is bent toward the falling position. In a case in which the coating member 54 is bent and the operation wire 26 is inserted at a position of the center axis CA of the coating member 54, a distance between a bent inside 54C of the inner periphery of the coating member 54 and the operation wire 26 is shorter than a distance between a bent outside 54D of the inner periphery of the coating member 54 and the operation wire 26. Since the coating member 54 is further bent in a case in which the curvature of the coating member 54 is further increased, there is a case in which the operation wire 26 and the bent inside 54C of the coating member 54 may be in contact with each other.

In this embodiment, as shown in FIG. 14, the operation wire 26 is inserted at a position offset to the bent outside 54D from the center axis CA of the coating member 54 in a radial direction. Since the operation wire 26 is offset from the center axis CA in the radial direction, a distance between the operation wire 26 and the coating member 54 can be ensured even in a case in which the coating member 54 is bent. Accordingly, the operation wire 26 and the coating member 54 are spaced apart from each other. Since the contact between the operation wire 26 and the coating member 54 can be avoided, damage to the inner periphery of the coating member 54 can be prevented.

For example, in a case in which a positioning member 82 into which the operation wire 26 is to be inserted is used on the lead-out side of the operation wire-guide passage 46 as shown in FIG. 14, the operation wire 26 can be offset from the center axis CA of the coating member 54 in a predetermined direction by a predetermined distance.

Next, another aspect in which the contact between the coating member and the operation wire is avoided will be described. There is a case in which the coating member 54 and the operation wire 26 are in contact with each other in a case in which the coating member 54 and the operation wire 26 are bent as described above. Accordingly, it is preferable that the coating member 54 and the operation wire 26 are linearly moved relative to each other between the standing position and the falling position of the standing base 50. In a case in which the coating member 54 and the operation wire 26 are linearly moved relative to each other, the contact between the coating member 54 and the operation wire 26 can be avoided. Therefore, damage to the inner periphery of the coating member 54 can be prevented.

Figure 15:
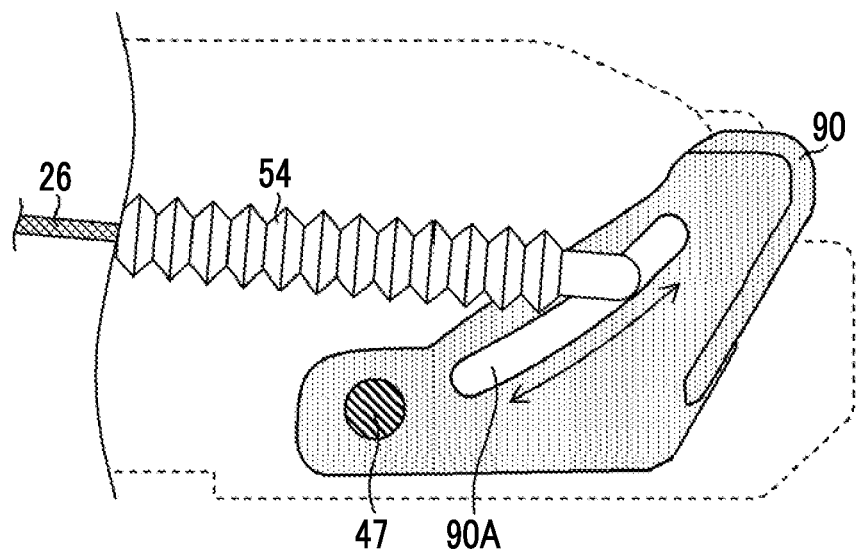
FIG. 15 is an enlarged view of an operation wire, a coating member, and a standing base.

FIG. 15 is an enlarged view of a coating member 54, an operation wire 26, and a standing base 90. As shown in FIG. 15, in this embodiment, a cam groove 90A is formed in the standing base 90 as the operation wire-mounting hole. The cam groove 90A has the shape of an arc that has a center close to the side of the standing position of the standing base 90. While the standing base 90 is rotated between the standing position and the falling position, the operation wire 26 can be moved along the cam groove 90A. Since the relative movement between the coating member 54 and the operation wire 26 is converted into a linear reciprocating motion by the cam groove 90A, the standing base 90 can avoid the contact between the coating member 54 and the operation wire 26. The linear reciprocating motion may be a linear motion that allows the contact between the coating member 54 and the operation wire 26 to be avoided. Accordingly, damage to the inner periphery of the coating member 54 can be prevented.

It is preferable that the tip of the operation wire 26 is closed by the coating member 54 as shown in FIG. 6 in a case in which the standing base 90 includes the earn groove 90A.

Figure 16:
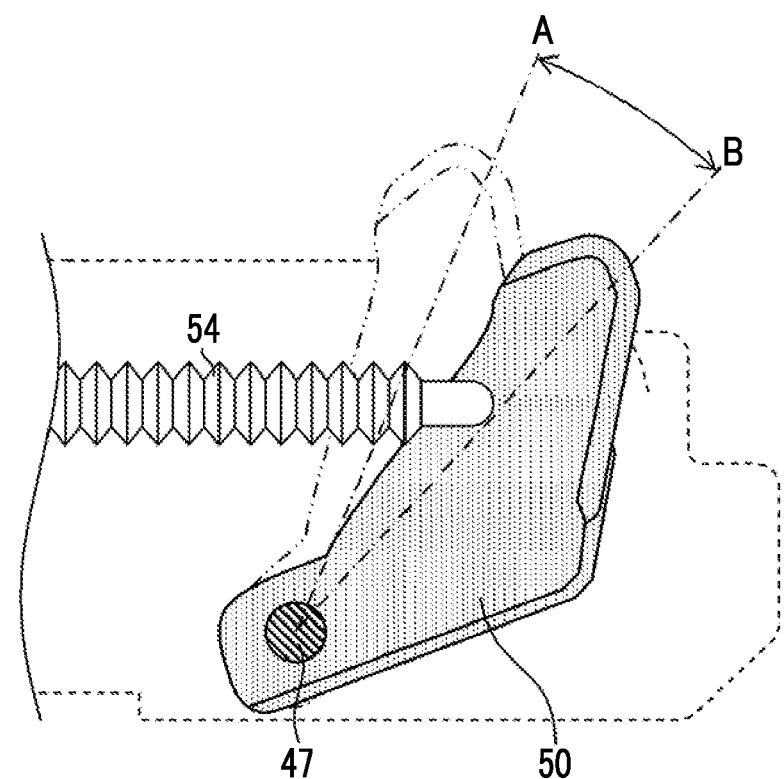
FIG. 16 is an enlarged view of another aspect of the operation wire, the coating member, and the standing base.

FIG. 16 is an enlarged view of a standing base 50 that allows the coating member 54 and the operation wire 26 to move linearly. In this embodiment, as shown in FIG. 16, the rotation range of the standing base 50 between a standing position A and a falling position B is in the range of, for example, about 15° to 30°. In a case in which the rotation range of the standing base 50 is in the range of 15° to 30°, the relative movement between the coating member 54 and the operation wire 26 can be converted into the linear reciprocating motion of the coating member 54 and the operation wire 26. Accordingly, the contact between the coating member 54 and the operation wire 26 can be avoided. The lead-out direction of the treatment tool 80 (not shown) can be controlled even though the rotation range of the standing base 50 is the above-mentioned range.

Figure 17:
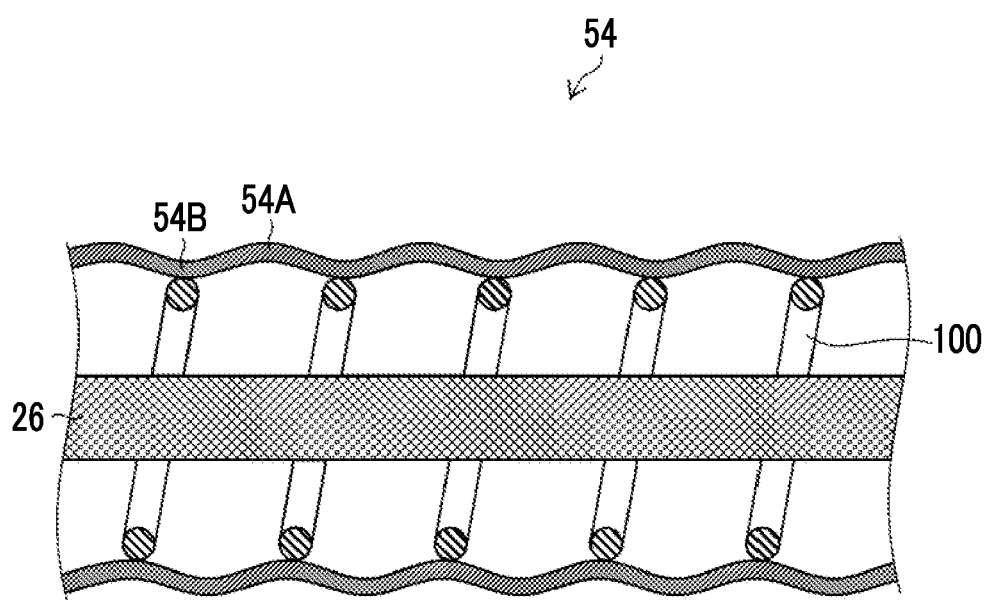
FIG. 17 is a cross-sectional view of a stretched coating member having a bellows structure.
Figure 18:
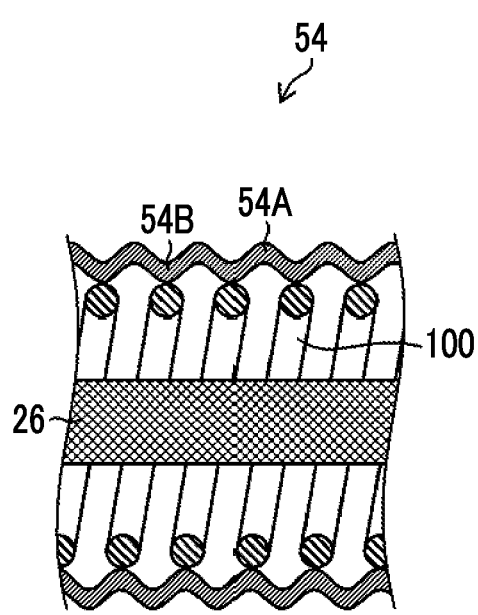
FIG. 18 is a cross-sectional view of the contracted coating member having the bellows structure.

FIG. 17 is a cross-sectional view of a stretched coating member having a bellows structure, and FIG. 18 is a cross-sectional view of the contracted coating member having the bellows structure. As shown in FIGS. 17 and 18, the coating member 54 has a bellows structure in which a large-diameter portion 54A and a small-diameter portion 54B are repeated. The coating member 54 is formed of a resin member.

The operation wire 26 is inserted into the coating member 54. In this embodiment, a coil spring 100 is disposed at a position where the coil spring 100 surrounds the operation wire 26, and the coating member 54 is mounted so as to be in contact with the outer periphery of the coil spring 100. As shown in FIGS. 17 and 18, the small-diameter portions 54B of the coating member 54 are in contact with the outer periphery of the coil spring 100. As shown in FIG. 18, the small-diameter portions 54B of the coating member 54 are in contact with the outer periphery of the coil spring 100. The large-diameter portions 54A of the coating member 54 are formed so as to protrude to the outer periphery of the coil spring 100 in a case in which the coating member 54 is contracted. The coil spring 100 means a spring that is formed by winding a metal wire in a cylindrical shape or the like.

Since the coil spring 100 is disposed as shown in FIGS. 17 and 18, the contact between the coating member 54 and the operation wire 26 can be avoided while the standing base 50 (not shown) is rotated to the falling position from the standing position by the operation wire 26. Accordingly, damage to the inner periphery of the coating member 54 can be prevented.

EXPLANATION OF REFERENCES

- 10: endoscope
- 12: insertion unit
- 14: operation unit
- 16: universal cord
- 18: tip portion
- 20: bendable part
- 22: soft part
- 24: treatment tool-insertion channel
- 26: operation wire
- 28: angle knob
- 30: operation lever
- 32: air/water supply button
- 34: suction button
- 36: treatment tool inlet
- 40: tip portion body
- 42: tip cap
- 42A: opening window
- 42B: partition wall
- 42C: slit
- 44: receiving chamber
- 44A: first chamber
- 44B: second chamber
- 45: treatment tool-guide passage
- 46: operation wire-guide passage
- 47: shaft portion
- 48: partition wall
- 50: standing base
- 50A: through hole
- 50B: hole
- 50C: through hole
- 50D: tapered surface
- 50E: guide surface
- 52: connection portion
- 54: coating member
- 54A: large-diameter portion
- 54B: small-diameter portion
- 54C: bent inside
- 54D: bent outside
- 56: recessed portion
- 58: tubular member
- 60: optical system-receiving chamber
- 62: illumination window
- 64: observation window
- 69: air/water supply nozzle
- 70: locking portion
- 80: treatment tool
- 82: positioning member
- 90: standing base
- 90A: cam groove
- 100: coil spring
- CA: center axis

What is claimed is:

1. An endoscope comprising:
an insertion unit that includes a tip and a base end;
a tip portion body that is provided on a tip side of the insertion unit;
a standing base that is adapted to be rotatable in a receiving chamber provided in the tip portion body;
an operation wire of which a tip side is connected to the standing base;
an operation wire-guide passage that is provided in the tip portion body to guide the operation wire to be inserted into an internal space of the insertion unit to the standing base; and
a stretchable coating member that covers the operation wire so as to extend in an extending direction of the operation wire and so as to allow the operation wire to be relatively movable over the entire region from a connection portion between the standing base and the operation wire to the operation wire-guide passage,
wherein a tip of the coating member and the standing base are liquid-tightly fixed to each other and a base end of the coating member and the operation wire-guide passage are liquid-tightly fixed to each other, and
the coating member is disposed at a position where a moving path of the coating member caused by an operation of the standing base and a moving path of a treatment tool led from a treatment tool-guide passage provided in the tip portion body do not interfere with each other.

2. The endoscope according to claim 1,
wherein the coating member is disposed at a position that is offset from the moving path of the treatment tool by a distance equal to or longer than a distance exceeding an increase in a diameter of the coating member in a case in which the coating member is contracted.

3. The endoscope according to claim 1,
wherein the standing base is made to stand by an operation of the operation wire, and pinches the treatment tool by the tip portion body and the standing base.

4. The endoscope according to claim 1, further comprising
a tip cap that is detachably mounted on the tip portion body,
wherein the tip cap includes a partition wall partitioning a first chamber in which the standing base is disposed and a second chamber in which the coating member is disposed, and
the partition wall includes a slit communicating with the first chamber and the second chamber so that the coating member extending from the side of the standing base is movable with the rotation of the standing base.

5. The endoscope according to claim 1,
wherein the coating member is in a contracted state or has a natural length in a first rotation range from a standing position in the entire rotation range of the standing base, and is stretched in a second rotation range in which the coating member is rotated to a falling position from the first rotation range.

6. The endoscope according to claim 5,
wherein the first rotation range is a range of ½ to ⅔ of the entire rotation range from the standing position.

7. The endoscope according to claim 1,
wherein the coating member has a bellows structure in which a large-diameter portion and a small-diameter portion are repeated in an axial direction.

8. The endoscope according to claim 1, further comprising
a tubular member that protrudes around a lead-out side of the operation wire-guide passage, and wherein the base end of the coating member is liquid-tightly fixed to the tubular member.

9. The endoscope according to claim 1, wherein the tip of the coating member is closed and receives a tip of the operation wire.

10. An endoscope comprising:
an insertion unit that includes a tip and a base end;
a tip portion body that is provided on a tip side of the insertion unit;
a standing base that is adapted to be rotatable in a receiving chamber provided in the tip portion body;
an operation wire of which a tip side is connected to the standing base;
an operation wire-guide passage that is provided in the tip portion body to guide the operation wire to be inserted into an internal space of the insertion unit to the standing base; and
a stretchable coating member that covers the operation wire so as to extend in an extending direction of the operation wire and so as to allow the operation wire to be relatively movable over the entire region from a connection portion between the standing base and the operation wire to the operation wire-guide passage,
wherein a tip of the coating member and the standing base are liquid-tightly fixed to each other and a base end of the coating member and the operation wire-guide passage are liquid-tightly fixed to each other, and
the coating member and the operation wire are spaced apart from each other in a state in which the coating member is contracted.

11. The endoscope according to claim 10, wherein the standing base is made to stand by an operation of the operation wire, and pinches a treatment tool led from a treatment tool-guide passage by the tip portion body and the standing base.

12. The endoscope according to claim 10, wherein the operation wire is inserted at a position offset from a center axis of the coating member in a radial direction.

13. The endoscope according to claim 10, wherein the standing base includes an operation wire-mounting hole, the operation wire-mounting hole of the standing base is formed of a cam groove in which the operation wire is movable, and the coating member and the operation wire are linearly reciprocated while the standing base is rotated between a standing position and a falling position.

14. The endoscope according to claim 10, wherein the coating member includes a coil spring and a resin member that covers the coil spring and protrudes to an outer periphery of the coil spring in a case in which the resin member is contracted.

15. An endoscope comprising:
an insertion unit that includes a tip and a base end;
a tip portion body that is provided on a tip side of the insertion unit;
a standing base that is adapted to be rotatable in a receiving chamber provided in the tip portion body;
an operation wire of which a tip side is connected to the standing base;
an operation wire-guide passage that is provided in the tip portion body to guide the operation wire to be inserted into an internal space of the insertion unit to the standing base; and
a stretchable coating member that covers the operation wire so as to extend in an extending direction of the operation wire and so as to allow the operation wire to be relatively movable over the entire region from a connection portion between the standing base and the operation wire to the operation wire-guide passage,
wherein a tip of the coating member and the standing base are liquid-tightly fixed to each other and a base end of the coating member and the operation wire-guide passage are liquid-tightly fixed to each other,
the coating member is disposed at a position where a moving path of the coating member caused by an operation of the standing base and a moving path of a treatment tool led from a treatment tool-guide passage provided in the tip portion body do not interfere with each other, and
the coating member and the operation wire are spaced apart from each other in a state in which the coating member is contracted.

* * * * *